United States Patent [19]
Baker

[11] 4,316,462
[45] Feb. 23, 1982

[54] FILTERING DEVICE FOR AN INJECTION DEVICE

[75] Inventor: John W. Baker, Flemington, N.J.

[73] Assignee: Siloam, Inc., Three Bridges, N.J.

[21] Appl. No.: 151,808

[22] Filed: May 21, 1980

[51] Int. Cl.³ .............................................. A61M 5/00
[52] U.S. Cl. ................................. 128/218 N; 128/221
[58] Field of Search ............... 128/218 R, 218 N, 215, 128/221, 214 R, 272.1; 141/1, 2

[56] References Cited

U.S. PATENT DOCUMENTS

| | | | |
|---|---|---|---|
| 2,626,603 | 1/1953 | Gabriel | 128/218 N |
| 3,008,570 | 11/1961 | Roehr et al. | 128/218 N X |
| 3,306,291 | 2/1967 | Burke | 128/218 R |
| 4,137,917 | 2/1979 | Cohen | 128/218 R |
| 4,180,071 | 12/1979 | Oiwa | 128/218 N |

Primary Examiner—John D. Yasko
Attorney, Agent, or Firm—Lerner, David, Littenberg & Samuel

[57] ABSTRACT

A filtering device for an injection device which includes a syringe and a needle affixed to the syringe. The filtering device comprises an elongated hollow tubular element mounted on the medical injection device to surround and sealingly enclose the needle. The end of a tubular element remote from the tip of the needle is open for the introduction of fluids therethrough into the hollow interior of the tubular element. A nonfiber releasing filtering member for filtering fluids is provided which includes a central filtering portion corresponding in size to the size of the opening of the end of the tubular element and outer peripheral portion surrounding the central filtering portion. A securing sleeve is provided for securing the filtering member to the tubular element at the open end thereof. The sleeve is mounted to the tubular element at the end thereof remote from the syringe, and the sleeve and the tubular element include respective mating surfaces for securing the peripheral portion of the filtering member between the sleeve and of the tubular element. In this manner, only filtered fluids will be drawn into the hollow interior of the tubular element through the open end thereof. The tubular element is removably mounted on the injection device so as to be removable therefrom to expose the needle after filtered fluid has been introduced into the syringe.

47 Claims, 12 Drawing Figures

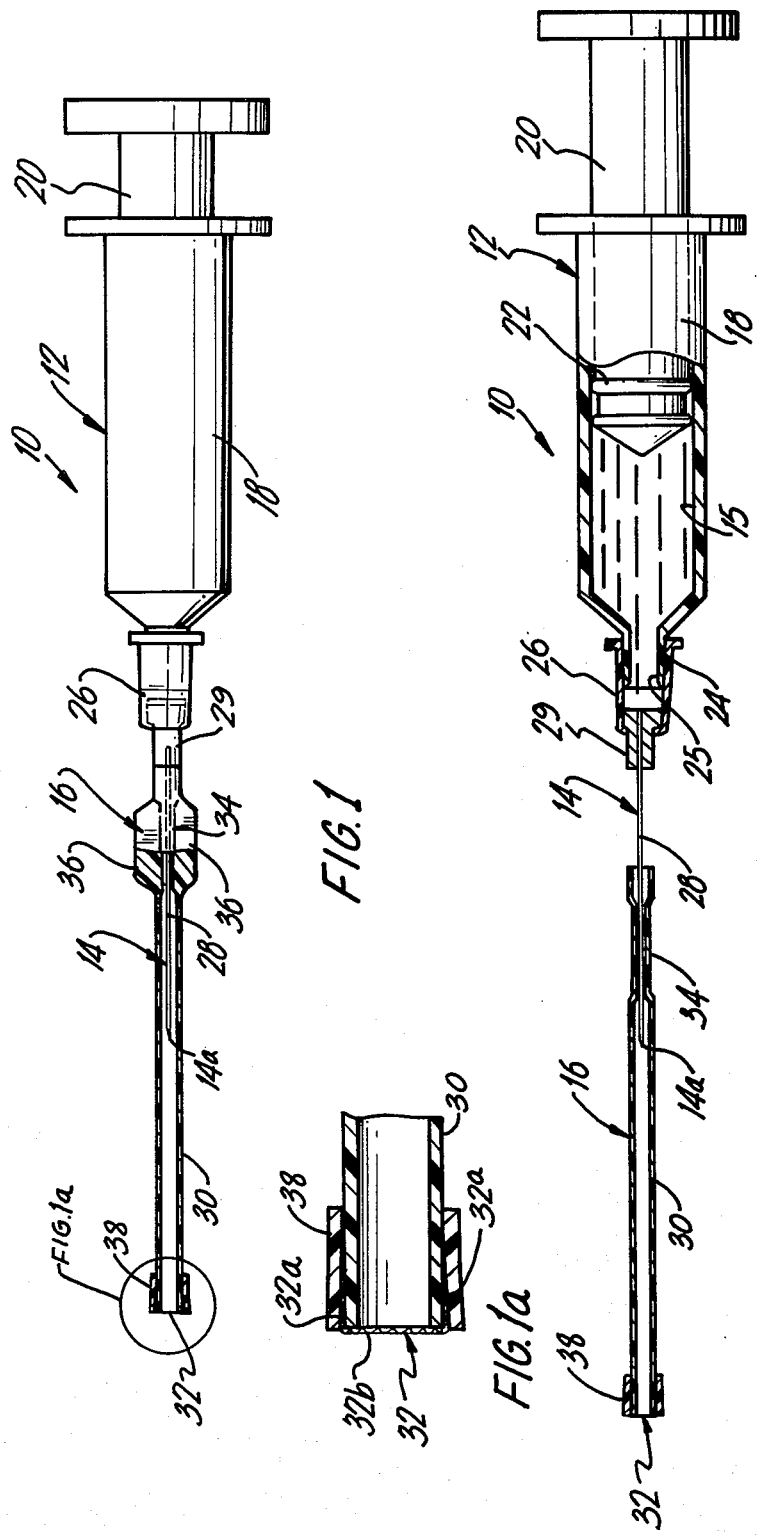

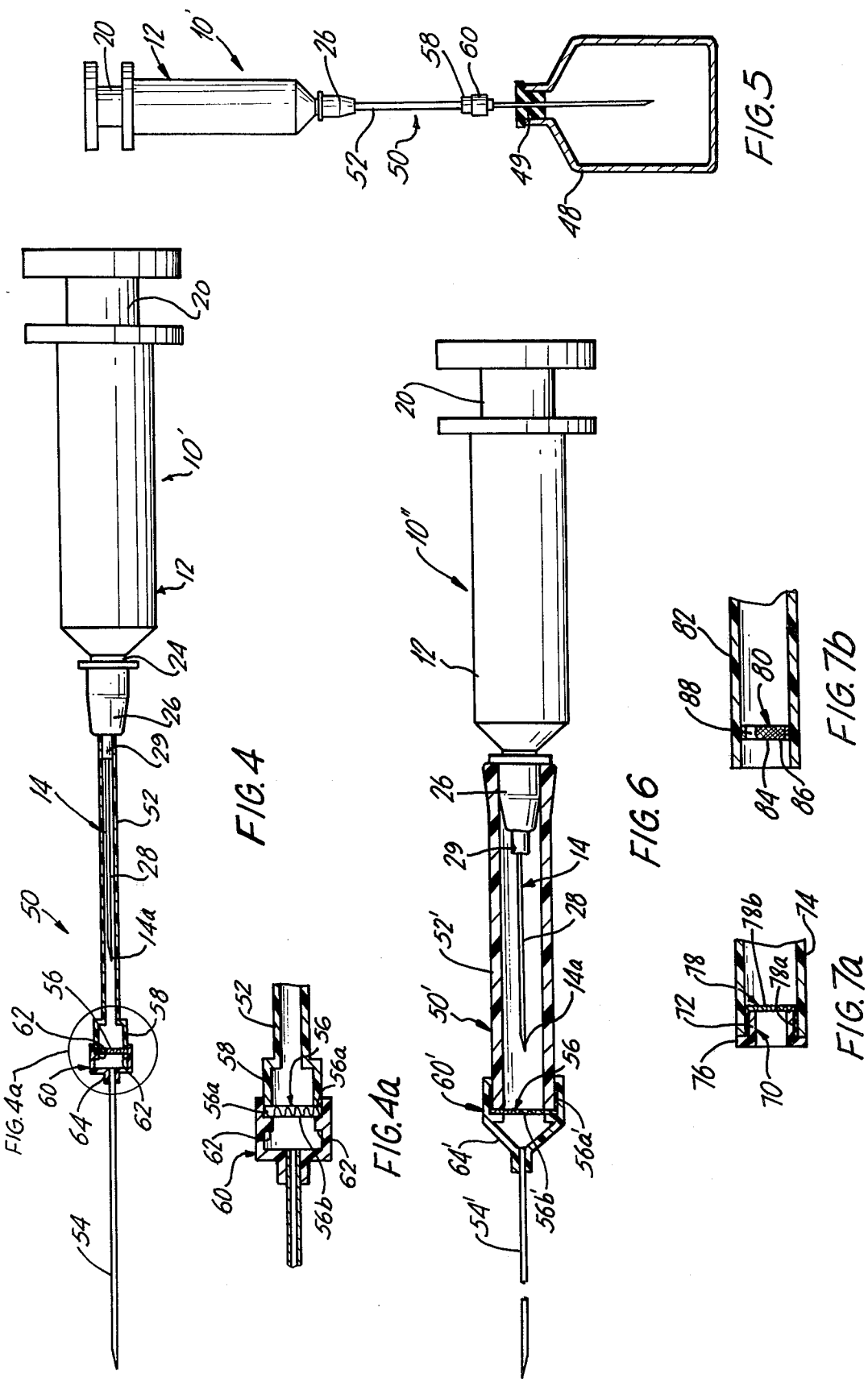

FILTERING DEVICE FOR AN INJECTION DEVICE

BACKGROUND OF THE INVENTION

The present invention relates to a filtering device for an injection device, and more particularly to a filtering device which provides for the introduction of filtered fluid into the injection device and subsequent injection of same into a patient or dispensing device without the necessity of having to remove and change needles between the drawing of fluids into the syringe and the injection of same.

One type of prior art filtering device for medical injection devices uses a first needle attached to the end of a syringe which has as an integral part thereof a filter medium, generally located adjacent the base of the needle when it is attached to the syringe, for the drawing of fluid through the filter needle and introducing same into the syringe. After the fluid has been aspirated through the filter needle, the needle with the filter is then removed and a second new needle is attached prior to injection of the fluid in the syringe into the patient or animal, or into a dispensing device. This product and arrangement has many objections, one of which is the fact that it requires a second needle and a product manipulation which has the potential of breaking sterile conditions. That is, with this arrangement one needle must be removed and replaced with a second needle, thus breaking or interrupting the supposedly sterile fluid path (i.e. between the needle and the syringe). Further, one of the greatest dangers with this type of arrangement is that the practitioner will forget to change needles and thus possibly inject into the patient a bolus or mass of particulates which have accumulated on the filter within the needle. For this latter reason, most hospitals have not allowed the use of filter needles outside the pharmacy.

Another type of product which has been used in the past comprises a filter tube which comprises a plastic tube having a hub portion with the filter medium therein. The hub is attached to the syringe and fluid is aspirated through the hub (where it is filtered) into the syringe. The filter tube is then removed and a needle attached to the syringe for subsequent injection of the fluid to the patient or into an intravenous bottle. This arrangement and product also has several disadvantages, among which include the fact that the filter tube must be removed and a needle attached before fluid can be injected. Such a manipulation can easily result in the breaking of a sterile technique or conditions in the fluid path. Still further, this arrangement requires that a needle be made available as a separate item of attachment.

A still further product which has been used in the past combines a needle with a second removable hub containing the filter, the hub being located at the end of the needle remote from the syringe. After aspirating the fluid through the needle/filter hub assembly and into the syringe, the practitioner is then required to disassemble the filter hub from the needle and the syringe, and then connect the needle to the syringe. In addition to the obvious manipulation which is required with this product and arrangement, there is also the potential for the needle to be contaminated with particulates.

Another device of the prior art is disclosed in U.S. Pat. No. 4,180,071 to Oiwa for a "Device for Withdrawing Injection Solutions", which is particularly adapted for use with solution containing ampuls which generally contain a solution sufficient for one injection only and which ampuls include a neck which is adapted to be cut and broken off to provide access to the solution therein or for withdrawing same into the syringe. In the arrangement disclosed in this reference, there is provided a tube whose length is such that when it is intimately fitted at its one end to the base portion of an injection needle, a filter medium, packed in the other or forward end of the tube, will be positioned slightly in front of the tip of the needle. The filter medium, which is disclosed as comprising a mass of fine fibers of polyester, polypropylene, polyamide or the like, is packed in the forward end of the tube and retained thereinplace by means of internal projections at each of the opposite ends of the portion of the filter medium to render the inserted filter medium somewhat retainable by the projections. In this arrangement, the portion of the tube around the filter medium is compressed by means of hot pressing or by permanently deforming the tube so that the filtered medium eventually has a multiplicity of pores ranging from preferably 3 to 5 microns in diameter. In use, the tube with the filter medium therein is placed over the base portion of the injection needle and the front end of the tube is then immersed in a solution in the ampul and the solution then withdrawn into the barrel of the syringe in a usual fashion. Because of the vacuum produced in the tube in this action, the solution is caused to flow into the needle through the filter medium which serves to filter out glass fragments contained in the ampul. Upon completion of the withdrawal of the solution, the tube is then removed from the needle base portion to provide an injection in the usual manner.

While such an arrangement overcomes some of the above-noted problems of the other prior art, the particular device and arrangement shown in U.S. Pat. No. 4,180,071 also possesses a number of disadvantages. For example, the particular filter medium used in this reference comprises an unsupported mass of fibers which are compressed to provide a pore size ranging from 3 to 5 microns in diameter. These fibers can become dislodged from their position in the forward end of the tube and perhaps even contaminate the end of the needle, which as can be appreciated is very disadvantageous. Furthermore, it is not possible with such an arrangement to provide for pore sizes ranging down to as little as 0.22 microns in diameter, the general accepted limit for providing a completely sterilized filtering as generally contaminating organisms and particles are generally of a greater size than 0.22 microns in diameter. Still further, the arrangement as disclosed in the Oiwa reference is not applicable for use with closed vials of solution which contain a number of doses of fluid to be injected as such vials are generally provided with rubber stoppers to maintain the sterile conditions within the vial and which rubber stoppers are designed to be pierced with a needle cannula to provide fluid communication with the solution in the vial; rather, the arrangement in the Oiwa reference requires an openable ampul. (It should be noted that the tapered end of the tube in the Oiwa arrangement does not comprise a needle cannula).

SUMMARY OF THE INVENTION

These and further disadvantages of the prior art are overcome with the improved filtering device of the present invention in which there is provided an elongated hollow tubular element having a first end and a second end with a hollow tubular body portion extending longitudinally therebetween. The first end of the tubular element includes mounting means for mounting the tubular member on the injection device to surround and sealingly enclose at least a portion of the needle within the tubular body portion. The second end of the tubular element is open for the introduction of fluids therethrough into the hollow interior of the tubular body portion. The longitudinal length of the tubular body portion is such that the second end is spaced from the end of the needle remote from this syringe when the tubular element is mounted on the injection device. Filtering means is provided for filtering of fluids drawn through the second end of the tubular element. The filtering means includes a central filtering portion corresponding in size to the size of the opening in the second end of the tubular element and an outer peripheral portion surrounding the central filtering portion. Sleeve securing means are provided for securing the filtering means to the tubular element at the second end thereof. The sleeve securing means is mounted to the tubular element at the second end, and the sleeve securing means and the tubular element include respective mating portions for securing the peripheral portion of the filtering means between the sleeve securing means and the tubular element so that only filtered fluid will be drawn into the tubular body portion through the opening in the second end of the tubular element to be introduced into the injection device. Also, the mounting means removably mounts the tubular element on the injection device so as to be removable therefrom to expose the needle after filtered fluid has been introduced into the syringe.

In this regard, it is important to note that the filtering means is positively secured in place at the second end of the tubular element by virtue of the peripheral portion thereof being secured in place between the respective mating portions of the sleeve securing means and of the tubular element. In a preferred embodiment, the respective mating portions of the sleeve securing means and the tubular element comprise side walls of the sleeve securing means and of the tubular element which are sized and shaped so as to telescopingly mate with one another and so that the peripheral portion of the filtering means is secured between such mating side walls.

In another preferred embodiment, one of the sleeve securing means and the tubular element is sized and shaped so that it is telescopingly received within the end of the other of the sleeve securing means and the tubular element, and the respective mating portions comprise the end surface of the one of the sleeve securing means and the tubular element, and a flange portion on the inner surface of the other of the sleeve securing means and the tubular element so that the peripheral portion of the filtering means is secured between the end surface and the flange portion.

In another aspsect of the present invention, the filtering device comprises an elongated tubular element having first and second ends, the first end including mounting means removably mounting the tubular element to the injection device and the second end being open for introduction of fluids therethrough and adapted to be spaced from the end of the needle remote from the syringe when the tubular element is mounted on the injection device. Filtering means for filtering fluids drawn through the second end of the tubular element are also provided. In this aspect of the present invention, the filtering means includes a substantially planar central filtering portion and a rigidified peripheral side wall portion sized and shaped to engage and seal against the inner side wall of the tubular element at the second end so that only filtered fluid will be drawn into the tubular body portion. In this manner, the rigidified peripheral side portion of the filtering means allows for secure mounting of the filtering means in the second end of the tubular element.

In a still further aspect of the present invention, the filtering device includes an elongated hollow body having a first end and a second end, the first end including mounting means for removably mounting of the elongated hollow body on the injection device to sealingly enclose at least a portion of the needle within the hollow interior of the elongated hollow body, and the second end including piercing means thereat for piercing a closed vial having fluid therein to be injected by the injection device. The piercing means serves to pierce the vial to provide access to the fluid in the vial and to provide fluid communication into the hollow interior of the elongated hollow body. Filtering means are provided for filtering fluids drawn through the second end of the elongated body, the filtering means being supported in the hollow interior of the elongated hollow body between the second end and the end of the needle remote from the syringe so that only filtered fluid is introduced into the syringe. This aspect of the present invention is particularly useful for filtering of fluids which are initially stored in vials which ae closed, such as for example, by means of a rubber stopper.

In a preferred embodiment of this aspect, the piercing means comprises a needle cannula which is adapted to pierce through the rubber stopper to provide communication between the fluid in the vial and the interior of the tubular element with the filtering means interposed therebetween to filter out contaminating particulates.

Also, preferably the filtering means comprises a non-fiber releasing filtering medium which may have a pore size of 0.22 microns, or even as small as 0.01 microns, so that completely sterile fluid will be introduced into the syringe.

These and further advantages and characteristics of the present invention will be apparent from the following detailed description of which illustrates the preferred embodiments of the present invention.

BRIEF DESCRIPTION OF THE DRAWINGS

FIG. 1 is a side view, partly in section, illustrating a filtering device in accordance with the present invention mounted on an injection device.

FIG. 1a is an enlarged sectional view of a portion of FIG. 1, illustrating one embodiment for securing the filtering means to the tubular element of the filtering device.

FIG. 2 is a side view, partly in section, illustrating the filtering device of FIG. 1 (the filtering device having been rotated 90° about its axis from the position shown in FIG. 1) being withdrawn from the injection device after filtered fluid has been introduced into the syringe.

FIG. 4 is a side view, partly in section, illustrating a further embodiment of the filtering device in accordance with the present invention.

FIG. 4a is an enlarged section view of a portion of FIG. 4, illustrating another embodiment for securing the filtering means to the tubular element of the filtering device.

FIG. 5 is a side elevational view illustrating the manner in which the injection device provided with a filtering device in accordance with the present invention is used for withdrawing of fluid from a vial provided with a rubber stopper.

FIG. 6 is a side view, partly in section, of a still further embodiment of the filtering device in accordance with the present invention.

FIGS. 7a and 7b are enlarged sectional views, similar to the sectional views of FIGS. 1a and 4a, illustrating further embodiments for securing the filtering means to the tubular element.

DETAILED DESCRIPTION OF THE INVENTION

Figure 3A:
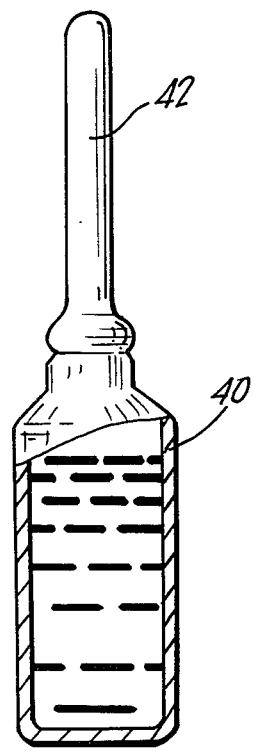
FIGS. 3a–3c illustrate an ampul and the manner in which an injection device provided with the filtering device in accordance with the present invention is used for withdrawing of fluid from the ampul into the injection device.

Referring now to the drawings wherein like reference characters represent like elements, there is shown in FIG. 1 a conventional medical injection device 10 comprising a syringe 12 having a needle 14 attached thereto, and a filter device 16 therefor for filtering and removing, bacteria and other micro organisms, as well as any other possible contaminating particulate matter contained in a solution of medicament before introduction of the solution into the syringe 12. As is conventional, the syringe 12 comprises a hollow, tubular barrel 18 which is open at its rearward end for receiving a plunger element 20 which is adapted for slideable movement within the hollow interior of the syringe barrel 18. An O-ring 22 may be provided at the forward end of the plunger element 20 to prevent any leakage of solution which has been drawn into the cavity 15 of the syringe 12 as the plunger 20 is withdrawn. The forward end of the syringe barrel 18 is provided with a male connector 24 having an opening 25 therethrough for drawing of a medicament into the syringe cavity 15.

The needle 14 may be secured to the syringe 12 in any conventional manner, such as for example, by means of a hollow hub 26 which carries the needle cannula 28 and which is removably mounted to the male connector 24 on the syringe 12. The needle cannula 28 includes a narrow passageway therethrough which communicates with the cavity 15 of the syringe 12 through the opening 25. In this manner, a solution or medicament may be drawn into the cavity 15 of the syringe 12 through the needle cannula 28 by withdrawing the plunger element 20, and subsequently be injected into a patient by depressing the plunger element 20 to expel the solution in the syringe 12 through the needle cannula 28.

In accordance with the present invention, the filter device 16 comprises an elongated, hollow, tubular element 30 which is provided with a filtering means 32 at one end thereof. The elongated, hollow, tubular element 30 has an inner diameter which is larger than the outer diameter of the needle cannula 28 and is adapted to be mounted to the medical injection device 10 so as to surround and enclose at least a portion of the needle cannula 28 thereof, with the filtering means 32 being spacedly positioned from the tip 14a of the needle cannula 28 (see FIG. 1). In this regard, as can be appreciated, the longitudinal length of the tubular element 30 preferably exceeds the length of the needle cannula 28 so that the tubular element 30 may surround and enclose the needle cannula 28 along the entire length of the needle cannula 28. This is advantageous since the tubular element 30 will thus serve to seal and protect the needle cannula 28 from any contamination or exposure before and during introduction of a solution into the syringe 12.

Preferably, the tubular element 30 is made of a suitable plastic material such as, for example, a polycarbonate material which may be transparent so that the needle cannula 28 may be easily viewed when surrounded by the tubular element 30.

In the embodiment shown in FIGS. 1 and 2, the plastic tubular element 30 includes a reduced section 34 at or near the rear or base end thereof which is adapted to tightly engage the outer surface of the needle cannula 28 and secure the tubular element 30 thereon. Alternatively, the rear or base end of the tubular element 30 could be mounted on the nose 29 of the needle hub 26 by means of an interference fit, or on the hub 26 itself and in engagement therewith to sealingly enclose the base portion of the needle cannula 28. Still further, other arrangements for mounting the tubular element 30 to the injection device 10 might comprise (i) providing a flexible or semi-rigid sheath on the needle cannula 28, the outer surface of which is then engaged by the inner surface of the tubular element 30; (ii) shrink fitting a band about the end of the tubular element 30 and the nose 29 of the needle 14 to hold the tubular element 30 in place (the shrink band having a pull away tab to release the tubular element 30 from the needle 14 when desired); (iii) providing an O-ring on the needle cannula 28 which is adapted to be engaged by the inner wall of the tubular element 30; or (iv) providing a molded element on a part of the needle 14 to which the tubular element 30 is secured in a suitable fashion. It should be appreciated of course that these are only a few of the ways the tubular element 30 may be mounted to the injection device 10, other ways being readily apparent to persons skilled in the art.

In the embodiment shown in FIGS. 1 and 2, the rear or base end of the tubular element 30 is provided a pair of protruding portions or wing members 36 on the outer surface thereof which advantageously aides in the mounting and removing of the tubular element 30 on the injection device 10. The reduced section 34 and the wing members 36 may conveniently be formed by a thermal forming operation to provide a section 34 of a reduced inner diameter adjacent the end of the tubular element 30 and, at the same time, form flattened wing members 36 on the outer surface of the tubular element 30 from the walls of the tubular element 30 at the location of the reduced section 34.

The forward end of the tubular element 30 is provided with a suitable filtering means 32 secured thereto. In the embodiment shown in FIGS. 1 and 2, the filtering means comprises a non-fiber releasing filtering medium 32 which has a dimension and configuration which is greater than the crosssectional dimension of the end of the tubular element 30 to provide a peripheral edge portion 32a which may be folded over the outer surface of the tubular element 30 and a central portion 32b inside the peripheral edge portion 32a forming the filtering portion for filtering of fluid to be introduced into the interior of the tubular element 30 (see FIG. 1a). The non-fiber releasing filtering medium 32 is placed over the end of the tubular element 30 and secured in place by means of a securing sleeve 38 which is forced over the end of the tubular element 30 to entrap the peripheral edges 32a of the filtering medium 32 between the inner surface of the sleeve 38 and the outer surface of the tubular element 30. The securing sleeve 38 preferably is comprised of a heat shrinkable polyolefin and has at at least one end an inner surface which is of a size and configuration to telescopingly mate with the outer side surface of the tubular element 30 with the edges 32a of the filtering medium 32 therebetween. The securing sleeve 38 is then heated and shrunk to mechanically secure the filtering medium 32 and securing sleeve 38 to the tubular element 30. Other arrangements for securing the securing sleeve 38 to the tubular element 30 to entrap the peripheral edge portion 32a therebetween could also be used, such as for example a stretchable rubber sleeve, an interference fit between the sleeve 38 and the tubular element 30, or cementing the sleeve 38 to the tubular element 30.

It should be noted in FIGS. 1 and 1a that the entire securing sleeve 38 is telescopingly received on the tubular element 30 so that the filtering medium 32 is located at the very end of the filtering device. However, if desired, the securing sleeve could be mounted so that it is only partially received on the end of the tubular element 30, with the filtering medium being disposed rearwardly thereof, and thus provide an entrance way for fluid to be introduced into the hollow interior of the tubular element 30.

As noted hereinabove, the inner diameter of the tubular element 30 along substantially its entire length is greater than the outer diameter of the needle cannula 28 to provide a chamber for receiving filtered fluid for subsequent introduction into the syringe 12. The reduced section 34 at the rearward end of the tubular element 30 provides a seal which prevents escape or leakage of solution from the hollow interior of the tubular element 30 as well as the drawing of any air, etc. into the hollow interior of the tubular element 30 which would not pass through the non-fiber releasing filtering medium 32. For example, if the needle cannula 28 of the injection device 10 comprises an 18-22 gauge cannula (this is a measure of the size of the passageway therethrough), the tubular element 30 may have an inner diameter of 0.105 inches and an outer diameter of 0.140 inches. However, these dimensions of the tubular element 30 may be suitably varied, for example to maximize the fluid flow through the filtering medium 32 into the hollow interior of the tubular element 30, as more fully discussed hereinbelow.

The non-fiber releasing filtering medium 32 is preferred as the fluid filtering means since it is non-fiber releasing and is available in a wide variety of suitable pore sizes; for example, from as low as approximately 0.22 microns, or even 0.01 microns in diameter, up to 5 microns and above. The non-fiber releasing aspect is most important, especially since the filtering device 16 is intended for use to filter medicaments for subsequent introduction into a patient or animal. If fibers or particles are released in the filtering device 16, the advantageous filtering characteristics would be destroyed. Further, as can be appreciated, it is preferable that the filtering medium 32 have relatively small pore sizes in order to filter out and remove particulate matter and organisms in the solution to be injected. In this regard, it is a generally accepted standard in the industry that filters having pores of 0.22 microns in diameter and smaller will provide a sterile solution as virtually all bacteria or other organisms and particulate matter which are desired to be removed are generally 0.22 microns in size or larger. Thus, it will be appreciated that if the filtering medium 32 used in the filter device of the present invention has a pore size of 0.22 microns and below, a substantially sterile solution will be provided. If desired, an even small pore size filtering medium could be employed, such as for example, a filtering medium 32 having pores of 0.01 microns in diameter, in which event the filtering medium would also be effective in filtering out many viruses. One preferred non-fiber releasing filtering medium 32 which may be used comprises a membrane or substrate of non-woven nylon coated with an acrylic co-polymer, such as is sold, for example, under the tradename Versapor Membrane by Gelman Science, Corp. Other non-fiber releasing filtering mediums could also be used, such as for example filtering mediums of nylon or polypropylene. While these filtering mediums are generally flexible, non-flexible mediums could also be used, such as for example a filtering medium made of a cellulose membrane. In this instance, the particular means for securing the filtering medium 32 to the tubular element 30 might have to be modified (see discussion hereinbelow respecting FIG. 7b).

Figure 3B:
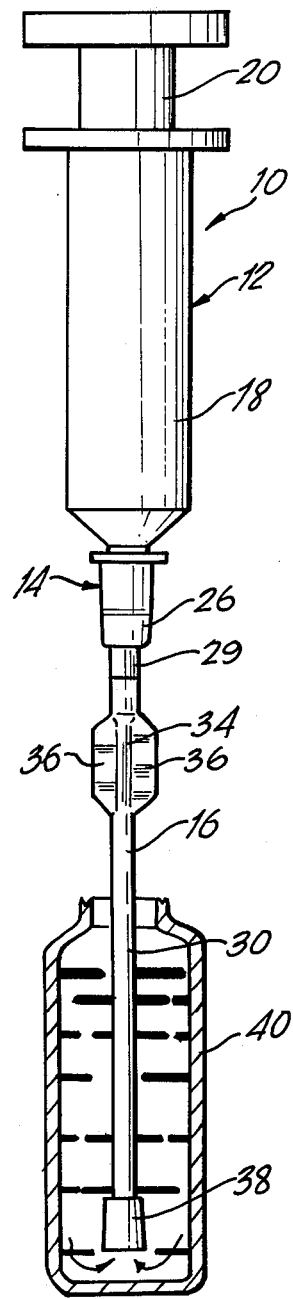
Figure 3C:
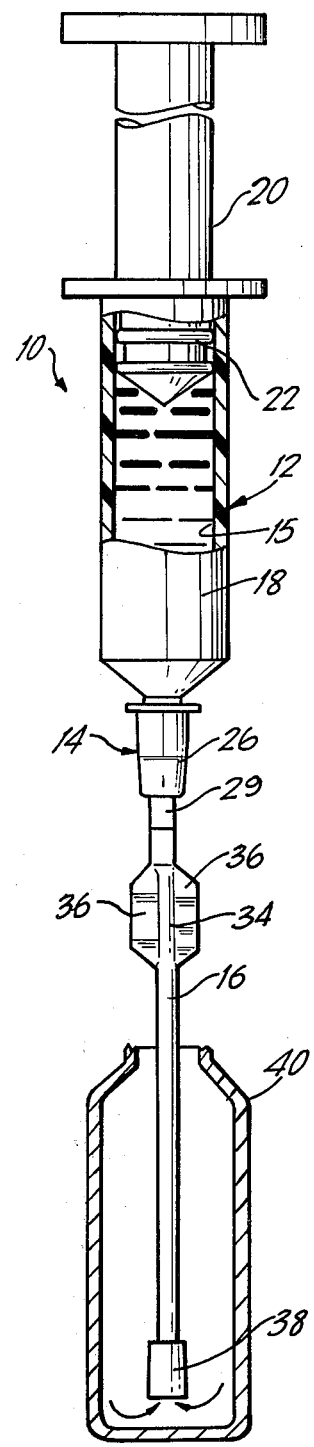

The filter device 16 and injection device 10, shown in FIGS. 1 and 2, are particularly useful with ampuls which generally contain a single dose of solution to be injected into a patient. Such an ampul 40, shown for example in FIG. 3a, generally includes an elongated neck 42 at the end thereof which serves to hermetically seal the solution within the ampul 40. When it is desired to provide an injection, the neck 42 of the ampul 40 is cut and broken off to provide access to the solution within the ampul 40. The filter device 16, initially assembled on the injection device 10 as shown in FIG. 1, is then manipulated to insert the end of the tubular element 30 into the ampul 40, as shown in FIG. 3b. The plunger element 20 on the syringe 12 is then withdrawn to create a vacuum within the tubular element 30 which serves to draw solution in the ampul 40 across the filtering medium 32 into the interior of the tubular element 30, and then into the syringe 12 through the needle 14. In this regard, since the end of the tubular element 30 is sealed against the needle 14, the vacuum created by withdrawal of the plunger 20 is maintained in the tubular element 30. Generally, since the ampul 40 only contains a single dose of medicament, the entire solution within the ampul 40 will be drawn into the syringe cavity 15 upon withdrawal of the plunger 20. The position of the plunger 20 after this operation is as shown in FIG. 3c. The injection device 10 and filter device 16, still assembled, are then withdrawn from the ampul 40. The filter device 16 is then removed from the injection device 10 by pulling the tubular element 30 away from the syringe 12, such as, for example, by grasping the wing members 36. This is shown in FIG. 2. During this operation, however, the needle 14 remains affixed to the syringe 12. After removal of the tubular element 30, the syringe 12 and needle 14 are then ready for injection of the solution in the syringe 12 into the patient in a conventional manner.

It will be appreciated in this regard, that the entire solution in the ampul 40 is introduced into the syringe after having passed through the filtering medium 32 provided in the end of the tubular element 30, thus insuring that the solution will be filtered before passing into the syringe 12, and thus filtering and removing all organisms and particulate matter which can not pass through the filtering medium 32. As noted above, if a filtering medium 32 having 0.22 micron size pores is provided, a substantially sterile solution or medicament will be provided.

It will be appreciated that in accordance with the present invention the requirement experienced in much of the prior art of having to change needles (thereby interrupting the sterile technique) is avoided with the present invention since the needle 14 on the syringe 12 always remains in place on the syringe 12 during both the drawing of fluid into the syringe 12 and subsequent injection of the fluid into the patient. That is, no changing of needles 14 is necessary. Also, with the present invention, only filtered fluid is received by the needle 14, thus avoiding the possibility of any particulate matter accumulating on the tip 14a of the needle cannula 28 or between the needle cannula 28 and the syringe 12. Furthermore, it will be appreciated that practitioners will not easily forget to remove the filtering device 16 on the needle 14 and syringe 12 since it would not be possible to inject the tubular element 30 into the patient. Rather, the practitioner will naturally and easily remove the tubular element 30 without interrupting or manipulating the fluid path, thus maintaining the sterile technique. In this regard, it is to be noted that the removal of the tubular element 30 involves both a convenient and an easy manipulation, and thus will be readily performed by practitioners.

One of the distinct advantages of the filtering medium 32 and the means of securement thereof to the tubular element 30 in accordance with the present invention is the fact that a wide variety of sizes for the filtering medium 32 may be utilized while still insuring positive securement and placement of the filtering medium 32 relative to the needle 14 on the syringe 12. In this regard, when smaller pore size filtering mediums 32 are used, for example, 0.22 microns and below, in order to easily be able to draw fluid therethrough for introducing fluid into the syringe 12, a larger filtering area may be desired in order to maintain a sufficient volume of flow during the drawing of fluid into the syringe 12. That is, with the smaller filter sizes, the resistance to flow therethrough is greatly increased. In order to maintain a sufficient volume of flow during withdrawal of the plunger 20, it may be desired to provide a larger cross-sectional area for the filtering medium 32. With the arrangement of the present invention for securing the filtering medium 32 to the tubular element 30, this can be easily accomplished as, for example, by providing an enlarged section at the end of the tubular element 30 where the filtering medium 32 is located. This enlarged area, for example, could be provided by a sleeve or cap member secured or bonded to the end of the tubular element 30 and having a larger cross-sectional area than that of the tubular element 30, and then securing the filtering medium 32 to the enlarged cross-sectional area with a second sleeve member. (One example of this arrangement is shown in FIG. 4, to be described more fully hereinbelow.) In this way, a small pore size filtering medium 32 can be utilized while still providing a desired volume of flow into the syringe 12 during drawing of the fluid into the syringe 12.

Still further, by positively securing the non-fiber releasing filtering medium 32 to the tubular element 30 in the manner in accordance with the present invention, it is possible to maintain the pore size of the particular non-fiber releasing filtering medium 32 chosen to insure the desired filtering characteristics associated with the chosen material. Although non-fiber releasing type filters have been utilized in the past with respect to injection devices, in these arrangements the non-fiber releasing filter was simply forced into a tube or straw and attached to the end of the injection device (without any needle being provided therein). However, in the forcing of the non-fiber releasing filter medium into the tube, the filter medium was often bunched and stretched, which had the effect of providing a larger pore size for the filter such that the same filtering characteristics would not be provided. That is, in the prior art when the non-fiber releasing filtering medium was pushed down into the tube, the pore size of the filtering medium opened up (which was desirable to provide for the same volume of flow during withdrawal of the plunger in the syringe); but this also had the effect of destroying the desired filtering characteristics associated with a small pore size non-fiber releasing filtering medium. On the other hand, by simply placing the non-fiber releasing filtering medium 32 over the end of the tubular element 30, in the manner in accordance with the present invention, the desired filtering characteristics of a particular non-fiber releasing filtering medium 32 are maintained and insured. Further, the filtering medium 32 is positively held in position and is not capable of movement or displacement in the present invention.

A second embodiment in accordance with the present invention which is particularly useful in connection with vials 48 or bottles of solution provided with rubber stoppers 49 (the rubber stoppers 48 being provided because such vials or bottles 48 generally contain more than a single dose of a solution for injection) is shown in FIGS. 4 and 4a. More particularly, FIG. 4 shows a similar medical injection device 10' comprised of a syringe 12 having a plunger 20 and a needle 13 secured to the male connector 24 of the syringe 12, and an alternative arrangement for the filtering device 50. In this embodiment, the filtering device 50 comprises an elongated hollow body 52 which is adapted at one end to be mounted on the injection device 10'. The opposite end of the hollow body 52 is provided with a piercing means 54 for piercing the rubber stopper 49 of a vial 48 of fluid and providing fluid communication with the hollow interior of the hollow body 52. A filtering medium 56 is provided in the hollow interior of the hollow body 52 intermediate the piercing means 54 (which may comprise a cannula) and the tip 14a of the injection needle cannula 28 so that fluid drawn into the syringe 12 will be filtered as described more fully hereinbelow.

In the embodiment shown in FIG. 4, the hollow body 52 comprises a tubular member or element which is adapted to be mounted at one end on the nose 29 of the needle hub 26. The opposite end of the tubular element 52 is provided with an enlarged end section or hub 58 to which the filtering medium 56 is secured, which enlarged end section 58 may be of a larger crosssectional area than that of the remaining portion of the tubular member 52. The enlarged end section 58 may, for example, be provided by means of a cylindrical cap having a reduced male connector bonded thereto, such as for example by heat sealing, or alternatively, the tubular member 52 could be formed with the enlarged hub 58 at the end thereof.

A securing sleeve member 60 and the filtering medium 56 are secured to this enlarged hub 58 in a manner similar to the manner in which the sleeve 38 and the filtering medium 32 are secured to the end of the tubular element 30 shown in FIG. 1. That is, the filtering medium 56 includes a central filtering portion 56b and a peripheral edge portion 56a surrounding the central filtering portion 56b, and is adapted to be placed over the enlarged hub 58 of the tubular member 52. As best seen in FIG. 4a, the central filtering portion 56b corresponds in size and shape to the hollow interior of the hub 58, and the peripheral portion 56a corresponds in size and shape to the end surface of the hub 58. The securing sleeve 60 has an inner surface which corresponds in size and shape to the outer surface of the hub 58 and further, is provided with flange portions 62 on the inner wall thereof spaced from the end of the securing sleeve 60. The securing sleeve 60 is forced or placed onto the end of the hub 58 to secure the peripheral edge portion 56a of the filtering medium 56 between the flange portions 62 of the securing sleeve 60 and the end surface of the hub 58. In this regard, the flange portions 62 also serve as a stop to limit the amount that the enlarged hub 58 is telescopingly received within the securing sleeve 60.

In this embodiment, the filtering medium 56 may comprise a non-flexible filtering medium, such as made for example of a cellular material, or may be flexible. If a flexible filtering medium 56 is employed, preferably the peripheral edge portion 56a is rigidified, such as for example by means of an epoxy cement, rubber adhesive, or the like.

The securing sleeve 60 also includes an end surface 64 opposite the end which receives the hub 58 to which the piercing means 54 is attached. In the embodiment disclosed, this piercing means comprises an introduction needle cannula 54, which may be either larger, smaller, or the same size as the needle cannula 28, depending on use. In the embodiment disclosed in FIG. 4, the introduction needle cannula 54 is slightly larger than the needle cannula 28, for example on the order of two needle gauges larger (i.e., if an 18 gauge needle cannula 28 is utilized, the introduction needle cannula 54 may comprise a 20 gauge cannula). The introduction needle cannula 54 is secured to the end 64 of the securing sleeve 60 in any suitable manner so as to be in fluid communication with the interior of the securing sleeve 60 and the filtering medium 56. This needle cannula 54 may comprise a plastic needle cannula, although it is more preferable that a metal needle cannula be utilized. The introduction needle cannula 54 includes a hollow interior passageway along its length so that fluid may be drawn thereinto and passed through the filtering medium 56 secured between the enlarged hub 58 and the securing sleeve 60.

The introduction needle cannula 54 is advantageously adapted to pierce through a rubber stopper 49 provided on the end of a vial 48 to provide access to the solution hermetically sealed therewithin. In this regard, as is conventional, the rubber stopper 49 is adapted to be pierced by a needle cannula and, when same is removed, to seal the opening through which the needle cannula passed to maintain the sterile conditions of the solution within the vial 48.

In use, the filtering device 50 shown in FIG. 4 is initially secured to the injection device 10' with at least a portion of the injection needle 14 being sealingly enclosed within the tubular member 52. The introduction needle 54 of the filtering device 50 is then used to pierce through the rubber stopper 49 of the vial 48 so as to be in fluid communication with the solution of medicament in the vial 48 (See FIG. 5). The plunger 20 on the syringe 12 is then withdrawn to draw the solution through the introduction needle cannula 54 and pass same through the filtering medium 56 into the interior of the tubular member 52, and from there through the injection needle 14 into the syringe 12. The introduction needle cannula 54 is then withdrawn from the vial 48 and the entire filter device 50 then removed from the injection device 10' to expose the injection needle 14 for subsequent injection of the solution in the syringe 12 into a patient or a dispensing device.

The arrangement providing an enlarged filtering area between the hub 58 and the securing sleeve 60 in the FIG. 4 embodiment is particularly useful in connection with a filtering medium 56 of a very small micron size, on the order of 0.22 microns and below, since it provides an enlarged area across which the solution to be filtered passes in order to maintain a sufficient desired volume of flow into the syringe 12 upon withdrawal of the plunger 20. For example, when a 0.22 micron filter medium is used, the inner diameter of the hub portion 58 which defines the filtering area may preferably be on the order of $\frac{1}{4}''$ with the inner diameter of the reduced elongated tubular section of the tubular member 52 being on the order of 0.105" and the outer diameter being on the order of 0.140". Also, it will be appreciated that the outer diameter of the tubular member 52 may be varied as desired for example to provide a thicker or more substantial wall for the tubular element 52 if desired. As will be appreciated, if a larger pore size filtering medium 56 is used, the size of this filtering section may be correspondingly reduced, if desired, while still maintaining the same desired volume of flow of solution into the syringe 12.

FIG. 6 shows a still further alternative arrangement for the filtering device 10'' which is also provided with a needle cannula 54' for piercing of a rubber stopper 49 on a vial or bottle 48 containing a medicament solution. In this arrangement, the tubular element 52' is provided with a substantially constant diameter along its entire length with the filtering medium 56' being secured over the end thereof by means of a conical or tapered sleeve member 60' which at its other end secures the introduction needle cannula 54'. Again, the size of the filtering area (corresponding to the size of the central filtering portion 56b') may be varied according to the pore size of the filtering medium 56' in order to provide and maintain a desired, sufficient volume of flow during withdrawal of the plunger 20 of the syringe 12. In this arrangement, the introduction needle cannula 54' is secured in the tapered end 64' of the securing sleeve 60' by any suitable method such as for example, by heat sealing.

Also, it will be noted that in the embodiment shown in FIG. 6, the rearward end of the tubular member 52' is mounted to the hub 26 which secures the injection needle 14 to the syringe 12. In this regard, the inner diameter of the tubular member 52' substantially corresponds to the outer diameter of the hub 26 so that a suitable seal is provided to maintain the vacuum within the tubular member 52' during withdrawal of the plunger 20, while at the same time providing ease in removal of the tubular member 52' from the injection device 10'' after the solution has been introduced into the syringe 12. However, as noted above, various other arrangements for this mounting could be utilized.

Although in each of the embodiments described hereinabove the securing sleeve 38 (60) is provided with an internal dimension and shape corresponding to the external dimension and shape of the tubular element or member 30 (52) for securing the filtering medium 32 (56) between the exterior of the tubular member 30 (52) and the interior of the securing sleeve 38 (60), it will be appreciated that the filtering medium 32 (56) could also be secured by means of a reduced size securing sleeve whose outer dimension and shape corresponds to the internal dimension and shape of the tubular member 30 (52) so that the peripheral portion 32a (56a) of the filtering medium 32 (56) will be secured between the interior surface of the tubular member 30 (52) and the exterior surface of the securing sleeve 38 (60). This is shown for example in FIG. 7a which is an enlarged sectional view of a further arrangement for securing the filtering means 32 (56) in place. Specifically, in this arrangement, the securing sleeve 70 includes a reduced male connector section 72 which is rigid and shaped to be telescopingly matingly received within the tubular element 74 at the end thereof remote from the syringe (not shown). An outwardly directed flange 76 is provided which is adapted to bear against the end surface of the tubular element 74. The filtering medium 78 again includes a central filtering portion 78b through which fluid to be filtered passes and a peripheral edge portion 78a which is trapped and secured in place between the outer surface of the reduced male connection section 72 and the inner surface of the tubular element 74 at the end remote from the syringe.

FIG. 7b shows a further alternative arrangement for securing a filtering means 80 in place at the end of the tubular element 82. In this embodiment, the filtering means 80 includes a substantially planar central filtering portion and a rigidified peripheral side wall portion 86, and is disposed with the tubular element 82 at the end thereof (a portion of the filtering means 80 has been broken away to illustrate a support ring 88 for forming the rigidified peripheral side wall portion 86, as more fully described below). The important feature in this embodiment is the rigidified peripheral side wall portion 86 of the filtering means 80 which serves to provide a suitable securement of the filtering means 80 with the inner wall of the tubular element 82. That is, by having a substantially rigid peripheral edge or side wall portion 86, positive securement and sealing of the filtering means 80 in the end of the tubular element 82 may be achieved to ensure that only filtered fluid is introduced into the tubular element 82 for subsequent introduction into the syringe (not shown).

This rigidified peripheral side wall portion 86 of the filtering means 80 may be obtained for example by use of a support ring 88 which is sized and shaped to mate with the inner surface of the tubular element 82 and to which a filtering medium 80 is mounted. The filtering medium 80 and support ring 88 may then be positioned inside the tubular element 82 at the end thereof with the side edges 86 of the filtering medium 80 held therein-place in a suitable manner. For example, an interference fit could be provided or alternatively, the end of the tubular element 82 could be heat shrunk after the filtering medium 80 and support ring 88 are properly positioned. Still further, the filtering medium 80 mounted and secured to the support ring 88 could be placed in an injection molding apparatus and the tubular element 82 then injection molded around the filtering medium 80 and support ring 88 to form a substantially integral one piece construction. In this regard, it should be noted that the purpose of the support ring 88 is to provide a rigid peripheral outer surface 86 for mating engagement and sealing with the inner wall of the tubular element 82. Thus, it will be appreciated that the support ring 88 is not necessary if the filtering medium 80 itself includes a rigid peripheral surface. For instance, the filtering medium 80 could comprise either a non-flexible filtering medium, such as a cellulose membrane, or could comprise a flexible filtering medium which has had its edges rigidified by a suitable treatment, such as by means of an epoxy cement, rubber adhesive, etc. Basically, the rigidity or stiffening of the flexible filtering medium 80 serves to provide a supportable filtering means 80 at the end of the tubular element 82. In any event, the fact that the filtering means 80 includes a rigidified peripheral side wall portion 86 allows for positive placement and subsequent sealing and securement of the filtering means 80 within the tubular element 82 at the end remote from the syringe, while at the same time providing for the use of a non-fiber releasing filtering medium 80.

Also, it will be appreciated that although circular tubular members 30 and securing sleeves 38 have been illustrated in the embodiments shown and described herein, different cross-sectional shapes could be utilized. In any event, the filtering medium 32 is positively secured in place at the end of the tubular element. For instance, triangular, rectangular, or even non-polygonal shapes could be employed.

Also, with the embodiments shown in FIGS. 4, 5 and 6 having introduction needle cannulas 54, it will be appreciated that because of the ease in removal of the filtering device 50 with the second needles 54 from the injection device 10, the risk of a practitioner failing to remove the introduction needle cannula 54 and tubular member 52 is minimized, especially in view of the fact that all that is required is a simple sliding of the filtering device 50 off the injection device 10 without the necessity of attaching another second needle thereto. In this regard, it may be desirable to provide some means for holding the tubular element 52 and cannula 54 in place on the injection device 10 during withdrawal of the cannula 54 from the rubber stopper 49 on the vial 48 (which acts as a source of frictional resistance) although this could be accomplished by simply holding the tubular element 52 and/or cannula 54 during the withdrawal step.

Further, because of the arrangement of the various components, it is anticipated that in use, the filtering devices 16 (50) and the injection needles 14 will be provided as separate assemblies which may simply be attached to a syringe 12. This has the advantage of maintaining the sterile conditions of the needle 14 prior to use. Alternatively, however, the filtering device 16 (50) and injection needle 14 could be provided as separate components and assembled to the syringe 12 just prior to use.

Accordingly, it will be appreciated that in accordance with the present invention there is provided an improved filtering device 16 (50) for an injection device 10 for filtering and removing organisms and other particulate matter from a solution of medicament to be injected into a patient. The filtering device 16 (50) comprises an elongated tubular member 30 (52) having a first end which is provided with means for mounting the tubular member 30 (52) on the injection needle 14 and/or syringe 12 to seal the end thereof and completely surround and enclose at least a portion of the needle cannula 28 within the hollow interior of the tubular member 30 (52). The second or other end of the tubular member 30 (52) is open. The filter device 16 (50) further includes filtering means 32 (56) which has a central filtering portion 32b (56b) and a peripheral portion 32a (56a) surrounding the central filtering portion 32b (56b). The filtering means 32, (56) is secured to the tubular member 30 (52) at the second end with a securing sleeve 38 (58). The securing sleeve 38 (60) is mounted on the tubular element 50 (52), and the securing sleeve 38 (60) and tubular element 30 (52) include respective mating portions for securing the peripheral portion 32a (66a) of the filtering means 32 (56) between the securing sleeve 38 (60) and the tubular element 30 (52) so that only filtered fluid will be introduced into the syringe 12. The entire assembly 16 (50) comprised of the tubular member 30 (52), the filtering means 32 (56) and the securing sleeve 38 (60) are removable from the injection device 10 after a solution has been drawn across the filtering means 32 (56) into the hollow interior of the tubular member 30 (52) and from there through the needle 14 into the syringe 12. Thus, after a filtered solution has been drawn into the syringe 12, the filtering device 16 (50) may be removed and the solution injected into the patient or dispensing device in a conventional manner.

In another aspsect of the present invention, the filtering device 16 (50) comprises an elongated tubular element 82 having first and second ends, the first end including mounting means removably mounting the tubular element 82 to the injection device 10 and the second end being open for introduction of fluids therethrough and adapted to be spaced from the end of the needle 14 remote from the syringe 12 when the tubular element 82 is mounted on the injection device 10. Filtering means 80 for filtering fluids drawn through the second end of the tubular element 82 are also provided. In this aspect of the present invention, the filtering means 80 includes a substantially planar central filtering portion 84 and a rigidified peripheral side wall portion 86 sized and shaped to engage and seal against the inner side wall of the tubular element 82 at the second end so that only filtered fluid will be drawn into the tubular body portion. In this manner, the rigidified peripheral side portion 86 of the filtering means 80 allows for secure mounting of the filtering means 80 in the second end of the tubular element 82.

In a still further aspect of the present invention, the filtering device 50 includes an elongated hollow body 52 having a first end and a second end, the first end including mounting means for removably mounting of the elongated hollow body 52 on the injection device 10 to sealingly enclose at least a portion of the needle 14 within the hollow interior of the elongated hollow body 52, and the second end including piercing means 54 thereat for piercing a closed vial 48 having fluid therein to be injected by the injection device 10. The piercing means 54 serves to pierce the vial 48 to provide access to the fluid in the vial 48 and to provide fluid communication into the hollow interior of the elongated hollow body 52. Filtering means 56 are provided for filtering fluids drawn through the second end of the elongated hollow body 52, the filtering means 56 being supported in the hollow interior of the elongated hollow body 52 between the second end and the end of the needle 14 remote from the syringe 12 so that only filtered fluid is introduced into the syringe. This aspect of the present invention is particularly useful for filtering of fluids which are initially stored in vials 48 which are closed, such as for example by means of a rubber stopper 49.

While the preferred embodiments of the present invention have been shown and described, it will be understood that such are merely illustrative and that changes may be made without departing from the scope of the invention as claimed.

What is claimed is:

1. A filtering device for an injection device which includes a syringe and a needle affixed to the syringe, said filtering device comprising:

an elongated hollow tubular element having a first end and a second end with a hollow tubular body portion extending longitudinally therebetween, said first end including mounting means for mounting said tubular element on said injection device to sealingly enclose at least a portion of said needle within said tubular body portion, said second end being open for the introduction of fluids therethrough into the hollow interior of said tubular body portion, and the longitudinal length of said tubular body portion being such that said second end is spaced from the end of said needle remote from said syringe when said tubular element is mounted on said injection device;

filtering means for filtering fluids drawn through said second end of said tubular element, said filtering means including a central filtering portion corresponding in size to the size of said opening at said second end of said tubular element and an outer peripheral portion surrounding said central filtering portion;

sleeve securing means for securing said filtering means to said tubular element at said second end, said sleeve securing means being mounted on said tubular element at said second end, and said sleeve securing means and said tubular element including respective mating portions for securing said peripheral portion of said filtering means between said sleeve securing means and said tubular element so that only filtered fluid will be drawn into said tubular body portion through said opening at said second end of said tubular element; and said mounting means mounting said tubular element on said injection device so as to be removable therefrom to expose said needle after filtered fluid has been introduced into said syringe.

2. The filtering device of claim 1 wherein said sleeve securing means and said tubular element are each sized and shaped to telescopingly mate with one another.

3. The filtering device of claim 2 wherein said respective mating portions of said sleeve securing means and of said tubular element comprise side walls of said sleeve securing means and of said tubular element which are sized and shaped to telescopingly mate with one another so that said peripheral portion of said filtering means is secured between said side walls of said sleeve securing means and of said tubular element.

4. The filtering device of claim 3 wherein said filtering means is positioned to overlie said second end of said tubular element and wherein the inner surface of said side wall of said sleeve securing means is sized and shaped to telescopingly, matingly receive the outer surface of said side wall of said tubular element at said second end.

5. The filtering device of claim 4 wherein said sleeve securing means comprises a sleeve having a first end for receiving said second end of said tubular element thereinto and a second end spaced from said second end of said tubular element when said sleeve is mounted on said second end of said tubular element.

6. The filtering device of claim 5 wherein said sleeve ring includes a stop on the inner surface thereof for engaging said second end of said tubular element to provide a stop for proper positioning of said sleeve securing means on said tubular element at said second end.

7. The filtering device of claim 4 wherein said sleeve securing means is bonded to said second end of said tubular element to entrap said peripheral portion of said filtering means between said inner surface of said side wall of said sleeve and said outer surface of said tubular element at said second end of said tubular element.

8. The filtering device of claim 2 wherein one of said sleeve securing means and said tubular element is telescopingly matingly received within the other of said sleeve securing means and said tubular element, and wherein said respective mating portions of said sleeve securing means and of said tubular element comprise the end surface of said one of said sleeve securing means and said tubular element and a flange portion on the inner surface of said other of said sleeve securing means and said tubular element, whereby said peripheral portion is secured between (i) said end surface of said one of said sleeve securing means and said tubular element and (ii) said flange portion of said other of said sleeve securing means and said tubular element.

9. The filtering device of claim 1 wherein said filtering means comprises a non-fiber releasing filtering medium.

10. The filtering device of claim 9 wherein said non-fiber releasing filtering medium has a plurality of pores of a size between 0.01 and 5 microns in diameter.

11. The filtering device of claim 10 wherein said non-fiber releasing filtering medium has pores of a size between 0.01 and 0.22 microns in diameter.

12. The filtering device of claim 1 wherein said mounting means slidably mounts said tubular element to said injection device adjacent to the location at which said needle is affixed to said syringe.

13. The filtering device of claim 12 wherein said needle includes a needle cannula and a needle hub for mounting said needle cannula on said syringe and wherein said mounting means slidably mounts said first end of said tubular element to said needle cannula adjacent said needle hub.

14. The filtering device of claim 13 wherein said mounting means comprises a reduced diameter section of said tubular element having a reduced diameter corresponding in size to the diameter of said needle cannula, said reduced diameter section being adjacent to said first end of said tubular element for slidably mounting said tubular element onto said needle cannula with said reduced portion encircling and sealing engaging a portion of said needle cannula.

15. The filtering device of claim 1 further including finger grips on said tubular element adjacent to said first end of said tubular element to aid in mounting and removing said tubular element on and from said injection device.

16. The filtering device of claim 1 wherein the cross-sectional size of said opening at said second end of said tubular element is at least as large as the inner cross-sectional size of said tubular element in the vicinity of the end of said needle which is remote from said syringe.

17. The filtering device of claim 2 wherein said sleeve securing means includes a first end for matingly engaging with said second end of said tubular element and a second end, and wherrein said filtering device further includes piercing means at said second end of said sleeve securing means for piercing a closed vial having fluid therein for injection by said injection device, said piercing means providing fluid communication therethrough with said first end of said sleeve securing means so that fluid may be introduced into said tubular body portion through said piercing means and through said filtering means.

18. The filtering device of claim 17 wherein said sleeve securing means includes a sleeve portion and an end wall at said second end, and wherein said piercing means comprises an introduction cannula mounted on said end wall of said sleeve securing means.

19. The filtering device of claim 17 wherein said tubular element includes an enlarged hub at said second end having a cross sectional size which is larger than the inner cross-sectional size of said tubular element in the vicinity of the end of said needle affixed to said syringe.

20. The filtering device of claim 19 wherein said sleeve securing means telescopingly matingly engages said enlarged hub.

21. The filtering device of claim 17 wherein said sleeve securing means comprises a sleeve portion and a tapered wall portion, and wherein said piercing means comprises an introduction cannula secured to said tapered wall portion.

22. A fluid injection device comprising:
a syringe having a cavity for holding a fluid therein;
a needle affixed to said syringe and being in fluid communication with said cavity and for introducing and expelling fluid from said cavity of said syringe; and
a filtering device for said needle and said syringe for filtering fluid to be introduced into said cavity, said filtering device including (1) a tubular element having a first end removably affixed to one of said syringe and said needle so that said tubular element surrounds and sealingly encloses within said tubular element at least the end of said needle remote from such syringe, and a second open end for receiving fluid to be introduced into said syringe cavity, said second end being displaced from said end of said needle remote from said syringe, (2) filtering means for said second end of said tubular element, said filtering means including a central filtering portion corresponding in size to the size of said opening at said second end of said tubular element and an outer peripheral portion surrounding said central filtering portion, and (3) sleeve securing means for securing said filtering means to said tubular element at said second end, said sleeve securing means being mounted on said tubular element at said second end, and said sleeve securing means and said tubular element including respective mating portions for securing said peripheral portion of said filtering means between said sleeve securing means and said tubular element so that only filtered fluid is drawn into said tubular element for introduction into said cavity of said syringe through said needle; and said tubular member being removable from said one of said syringe and said needle to expose said needle for expelling fluid from said cavity of said syringe.

23. The fluid injection device of claim 22 wherein said sleeve securing means and said tubular element are each sized and shaped to telescopingly mate with one another.

24. The fluid injection device of claim 23 wherein said respective mating portions of said sleeve securing means and of said tubular element comprise side walls of said sleeve securing means and of said tubular element which are sized and shaped to telescopingly mate with one another so that said peripheral portion of said filtering means is secured between said side walls of said sleeve securing means and of said tubular element.

25. The fluid injection device of claim 24 wherein said filtering means is positioned to overlie said second end of said tubular element and wherein the inner surface of said side wall of said sleeve securing means is sized and shaped to telescopingly, matingly receive the outer surface of said side wall of said tubular element at said second end.

26. The fluid injection device of claim 25 wherein said sleeve securing means is bonded to said second end of said tubular element to entrap said peripheral portion of said filtering means between said inner surface of said side wall of said sleeve securing means and said outer surface of said tubular element at said second end of said tubular element.

27. The fluid injection device of claim 22 wherein said filtering means comprises a non-fiber filtering medium.

28. The fluid injection device of claim 27 wherein said non-fiber releasing filtering medium has a plurality of pores of a size between 0.01 and 5 microns in diameter.

29. The fluid injection device of claim 28 wherein said non-fiber releasing filtering medium has pores of a size between 0.01 and 0.22 microns.

30. The fluid injection device of claim 22 wherein said first end of said tubular element is slidably mounted to said needle adjacent the location at which said needle is affixed to said syringe.

31. The fluid injection device of claim 30 wherein said needle includes a needle cannula, and wherein said tubular element includes a reduced diameter section having a reduced diameter corresponding in size to the diameter of said needle cannula, said reduced diameter section being adjacent to said first end of said tubular element for slidably mounting said tubular element onto said needle cannula with said reduced portion encircling and sealing engaging a portion of said needle cannula.

32. The fluid injection device of claim 23 wherein said sleeve securing means includes a first end for matingly engaging with said second end of said tubular element and a second end, and wherein said filtering device further includes piercing means at said second end of said sleeve securing means for piercing a closed vial having fluid therein for injection by said injection device, said piercing means providing fluid communication therethrough with said first end of said sleeve securing means so that fluid may be introduced into said tubular body portion through said piercing means and through said filtering means.

33. The fluid injection device of claim 32 wherein said sleeve securing means includes a sleeve portion and an end wall at said second end, and wherein said piercing means comprises an introduction cannula mounted on said end wall of said sleeve securing means.

34. The fluid injection device of claim 32 wherein said tubular element includes an enlarged hub at said second end having a cross-sectional size which is larger than the inner cross-sectional size of said tubular element in the vicinity of the end of said needle affixed to said syringe.

35. The fluid injection device of claim 34 wherein said sleeve securing means telescopingly, matingly engages said enlarged hub.

36. The fluid injection device of claim 32 wherein said sleeve securing means comprises a sleeve portion and a tapered wall portion, and wherein said piercing means comprises an introduction cannula secured to said tapered wall portion.

37. A filtering device for an injection device which includes a syringe and a needle affixed to the syringe, said filtering device comprising:

an elongated hollow body having a first end and a second end, said first end including mounting means for mounting said elongated hollow body on said injection device to sealingly enclose at least a portion of said needle within the hollow interior of said elongated hollow body with said second end of said elongated hollow body being spaced from the end of said needle remote from said syringe, said second end having an opening therethrough for introduction of fluids therethrough into the hollow interior of said elongated hollow body;

said second end of said elongated hollow body including piercing means for piercing a closed vial having a fluid therein to be injected by said injection device, said piercing means serving to pierce said vial to provide access to said fluid in said vial and to provide fluid communication into the hollow interior of said elongated hollow body for drawing fluid thereinto to be introduced into said syringe;

filtering means for filtering fluids drawn through said second end of said elongated hollow body;

support means for supporting said filtering means in the hollow interior of said elongated hollow body between said second end of said elongated hollow body and said end of said needle remote from said syringe so that only filtered fluid is introduced into said syringe; and said mounting means mounting said elongated hollow body on said injection device so as to be removable therefrom to expose said needle after filtered fluid has been introduced into said syringe.

38. The filtering device of claim 37 wherein said piercing means comprises an introduction cannula at said second end of said elongated hollow body.

39. The filtering device of claim 38 wherein said filtering means includes a central filtering portion corresponding in size to the size of said opening at said second end of said elongated hollow body and an outer peripheral portion surrounding said central filtering portion; wherein said support means comprises a securing sleeve mounted on said tubular element at said second end of said elongated hollow body for securing said peripheral portion of said filtering means between said sleeve securing means and said elongated hollow body so that only filtered fluid will be drawn into said hollow interior of said elongated hollow body through said filtering means at said second end.

40. The filtering device of claim 39 wherein said sleeve securing means and said elongated hollow body are each sized and shaped to telescopingly mate with one another, said sleeve securing means and said elongated hollow body including respective mating portions for securing said peripheral portion of said filtering means therebetween.

41. The filtering device of claim 40 wherein said respective mating portions of said sleeve securing means and of said elongated hollow body comprise side walls of said sleeve securing means and of said elongated hollow body which are sized and shaped to telescopingly mate with one another so that said peripheral portion of said filtering means is secured between said side walls of said sleeve securing means and of said elongated hollow body.

42. The filtering device of claim 40 wherein one of said sleeve securing means and said elongated hollow body is telescopingly matingly received within the other of said sleeve securing means and said elongated hollow body, and wherein said respective mating portions of said sleeve securing means and of said elongated hollow body comprise the end surface of said one of said sleeve securing means and said elongated hollow body and a flange portion on the inner surface of said other of said sleeve securing means and said elongated hollow body, whereby said peripheral portion is secured between (i) said end surface of said one of said sleeve securing means and said elongated hollow body and (ii) said flange portion of said other of said sleeve securing means and said elongated hollow body.

43. The filtering device of claim 37 wherein said filtering means comprises a non-fiber releasing filtering medium.

44. The filtering device of claim 43 wherein said non-fiber releasing filtering medium has a plurality of pores of a size between 0.01 and 5 microns in diameter.

45. A filtering device for an injection device which includes a syringe and a needle affixed to the syringe, said filtering device including:
an elongated hollow tubular element having a first end and a second end with a hollow tubular body portion extending longitudinally therebetween, said first end including mounting means for mounting said tubular element on said injection device to sealingly enclose at least a portion of said needle within said body portion, said second end being open for the introduction of fluids therethrough into the hollow interior of said tubular body portion, and the longitudinal length of said tubular body portion being such that said second end is spaced from the end of said needle remote from said syringe when said tubular element is mounted on said injection device;
filtering means for filtering fluids drawn through said second end of said tubular element, said filtering means including a substantially planar central filtering portion and a rigidified peripheral side wall portion sized and shaped to engage and seal against the inner side wall of said tubular element at said second end so that only filtered fluid will be drawn into said tubular body portion into said filtering means; and
said mounting means mounting said tubular element on said injection device so as to be removable therefrom to expose said needle after filtered fluid has been introduced into said syringe.

46. The filtering device of claim 45 wherein said filtering means comprises a non-fiber releasing filtering medium.

47. The filtering device of claim 46 wherein said non-fiber releasing filtering medium has a plurality of pores of a size between 0.01 and 5 microns in diameter.

* * * * *